(12) United States Patent
Vale

(10) Patent No.: US 11,872,354 B2
(45) Date of Patent: Jan. 16, 2024

(54) FLEXIBLE CATHETER SHAFT FRAME WITH SEAM

(71) Applicant: Neuravi Limited, Galway (IE)

(72) Inventor: David Vale, Galway (IE)

(73) Assignee: NEURAVI LIMITED, Galway (IE)

(*) Notice: Subject to any disclaimer, the term of this patent is extended or adjusted under 35 U.S.C. 154(b) by 192 days.

(21) Appl. No.: 17/183,444

(22) Filed: Feb. 24, 2021

(65) Prior Publication Data

US 2022/0265963 A1 Aug. 25, 2022

(51) Int. Cl.
*A61M 25/00* (2006.01)

(52) U.S. Cl.
CPC .... *A61M 25/0043* (2013.01); *A61M 25/0013* (2013.01)

(58) Field of Classification Search
CPC .......... A61M 25/0043; A61M 25/0013; A61M 2025/0059; A61M 25/0012; A61M 25/0051; A61M 2025/0024; A61M 25/0023; A61M 25/005; A61M 25/0054
See application file for complete search history.

(56) References Cited

U.S. PATENT DOCUMENTS

| | | |
|---|---|---|
| 4,243,040 A | 1/1981 | Beecher |
| 4,324,262 A | 4/1982 | Hall |
| 4,351,342 A | 9/1982 | Wiita et al. |
| 4,575,371 A | 3/1986 | Nordqvist et al. |
| 4,592,356 A | 6/1986 | Gutierrez |
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |

(Continued)

FOREIGN PATENT DOCUMENTS

| | | |
|---|---|---|
| CN | 1658920 A | 8/2005 |
| CN | 1972728 A | 5/2007 |

(Continued)

OTHER PUBLICATIONS

US 6,348,062 B1, 02/2002, Hopkins (withdrawn)

(Continued)

*Primary Examiner* — Amber R Stiles
*Assistant Examiner* — Phoebe Anne Staton
(74) *Attorney, Agent, or Firm* — TROUTMAN PEPPER HAMILTON SANDERS LLP

(57) ABSTRACT

The designs herein can be for a flexible and kink-resistant catheter with a support tube which can be radially expanded to enable it to be slid over an inner liner on a mandrel during assembly. The designs are flexible enough to allow the catheter to access remote vessel occlusions but also benefit from good compressive and tensile stiffness. The designs can have a laser cut frame with interlocking structure of circumferentially discontinuous rib struts. The discontinuities can be aligned to form at least one continuous axial seam which is separable to allow for the radial expansion during manufacturing. A series of polymeric outer jackets can coat or encapsulate the struts of the frame, giving variable stiffness and preventing disengagement of the interlocking structure while the catheter is pushed through tortuous anatomy.

9 Claims, 6 Drawing Sheets

(56) References Cited

U.S. PATENT DOCUMENTS

| | | |
|---|---|---|
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summers et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,846,251 A | 12/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,142,957 A | 11/2000 | Diamond et al. |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,407 B1 | 11/2001 | Zando-Azizi et al. |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. et al. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |

(56) References Cited

U.S. PATENT DOCUMENTS

| | | |
|---|---|---|
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder et al. |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |

(56) References Cited

U.S. PATENT DOCUMENTS

| | | |
|---|---|---|
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,610,668 B2 | 4/2020 | Burkholz et al. |
| 10,716,915 B2 | 7/2020 | Ogle et al. |
| 10,835,271 B2 | 11/2020 | Ma |
| 11,076,879 B2 | 8/2021 | Yee et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0144689 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbu |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059993 A1 | 3/2005 | Ramzipoor et al. |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119524 A1 | 6/2005 | Sckine et al. |
| 2005/0119668 A1 | 6/2005 | Teague et al. |
| 2005/0125024 A1 | 6/2005 | Sepetka |
| 2005/0131449 A1 | 6/2005 | Salahieh et al. |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0036271 A1 | 2/2006 | Schomer et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |

(56) References Cited

U.S. PATENT DOCUMENTS

| | | |
|---|---|---|
| 2007/0179513 A1 | 8/2007 | Deutsch |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239182 A1 | 10/2007 | Glines et al. |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0269774 A1 | 10/2008 | Garcia et al. |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0016957 A1 | 1/2010 | Jager et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavaski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Eynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |

(56) References Cited

U.S. PATENT DOCUMENTS

| | | |
|---|---|---|
| 2014/0188127 A1 | 7/2014 | Dubrul et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371777 A1 | 12/2014 | Rudakov et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173782 A1 | 6/2015 | Garrison et al. |
| 2015/0173783 A1 | 6/2015 | Tah et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0290437 A1 | 10/2015 | Rudakov et al. |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086864 A1 | 3/2017 | Greenhalgh et al. |
| 2017/0086996 A1 | 3/2017 | Peterson et al. |
| 2017/0239447 A1 | 3/2017 | Greenhalgh et al. |
| 2017/0095138 A1* | 4/2017 | Nakade ............... A61B 1/0052 |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0252043 A1 | 9/2017 | Fuller et al. |
| 2017/0252064 A1 | 9/2017 | Staunton |
| 2017/0259042 A1 | 9/2017 | Nguyen et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |

(56) References Cited

U.S. PATENT DOCUMENTS

| | | |
|---|---|---|
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193050 A1 | 7/2018 | Hawkins et al. |
| 2018/0193591 A1 | 7/2018 | Jaroch et al. |
| 2018/0235743 A1 | 8/2018 | Farago et al. |
| 2018/0256177 A1 | 9/2018 | Cooper et al. |
| 2018/0303610 A1 | 10/2018 | Anderson |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0247627 A1 | 8/2019 | Korkuch et al. |
| 2019/0255290 A1 | 8/2019 | Snyder et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2020/0214859 A1 | 7/2020 | Sherburne |
| 2020/0281611 A1 | 9/2020 | Kelly et al. |
| 2020/0353208 A1 | 11/2020 | Merhi et al. |
| 2020/0383698 A1 | 12/2020 | Miao et al. |
| 2021/0085935 A1 | 3/2021 | Fahey et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0219821 A1 | 7/2021 | Appling et al. |
| 2022/0117614 A1 | 4/2022 | Salmon et al. |
| 2022/0125450 A1 | 4/2022 | Sirhan et al. |
| 2022/0313426 A1 | 10/2022 | Gifford, III et al. |
| 2023/0054898 A1* | 2/2023 | Gurovich ............... A61F 2/966 |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 202009001951 U1 | 4/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| WO | WO 93/04722 A2 | 3/1993 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/018085 A2 | 3/2003 |
| WO | WO 03/030751 A1 | 4/2003 |
| WO | WO 03/051448 A2 | 6/2003 |
| WO | WO 2004/028571 A1 | 4/2004 |
| WO | WO 2004/056275 A1 | 7/2004 |
| WO | WO 2005/000130 A1 | 1/2005 |
| WO | WO 2005/027751 A1 | 3/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2009/019664 A1 | 2/2009 |
| WO | WO 2009/031338 A1 | 3/2009 |
| WO | WO 2009/076482 A1 | 6/2009 |
| WO | WO 2009/086482 A2 | 7/2009 |
| WO | WO 2009/103125 A1 | 8/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A1 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2014/188300 A1 | 11/2014 |
| WO | WO 2015/061365 A1 | 4/2015 |
| WO | WO 2015/134625 A1 | 9/2015 |
| WO | WO 2015/179324 A2 | 11/2015 |
| WO | WO 2015/179377 A1 | 11/2015 |
| WO | WO 2015/189354 A1 | 12/2015 |
| WO | WO 2016/010995 A1 | 1/2016 |
| WO | WO 2017/004234 A1 | 1/2017 |
| WO | WO 2017/097616 A1 | 6/2017 |
| WO | WO 2018/178979 A1 | 10/2018 |
| WO | WO 2018/193603 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/167653 A1 | 8/2021 |
| WO | WO 2022/020366 A2 | 1/2022 |

OTHER PUBLICATIONS

Struffert, T., et al. "Intravenous flat detector CT angiography for non-invasive visualisation of intracranial flow diverter: technical feasibility" Eur Radiol 21:1797-1801 (2011).

(56) References Cited

OTHER PUBLICATIONS

Partial European Search Report dated Jul. 15, 2022 issued in European Application No. 22 15 8145.

* cited by examiner

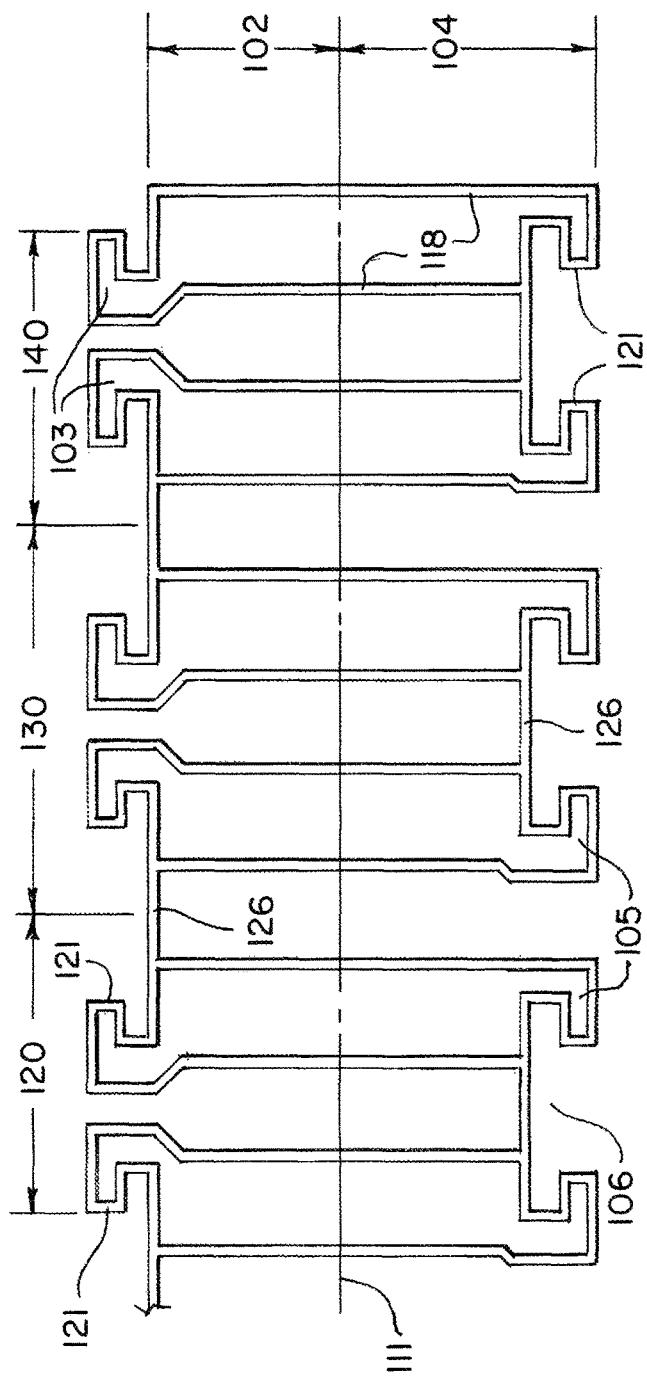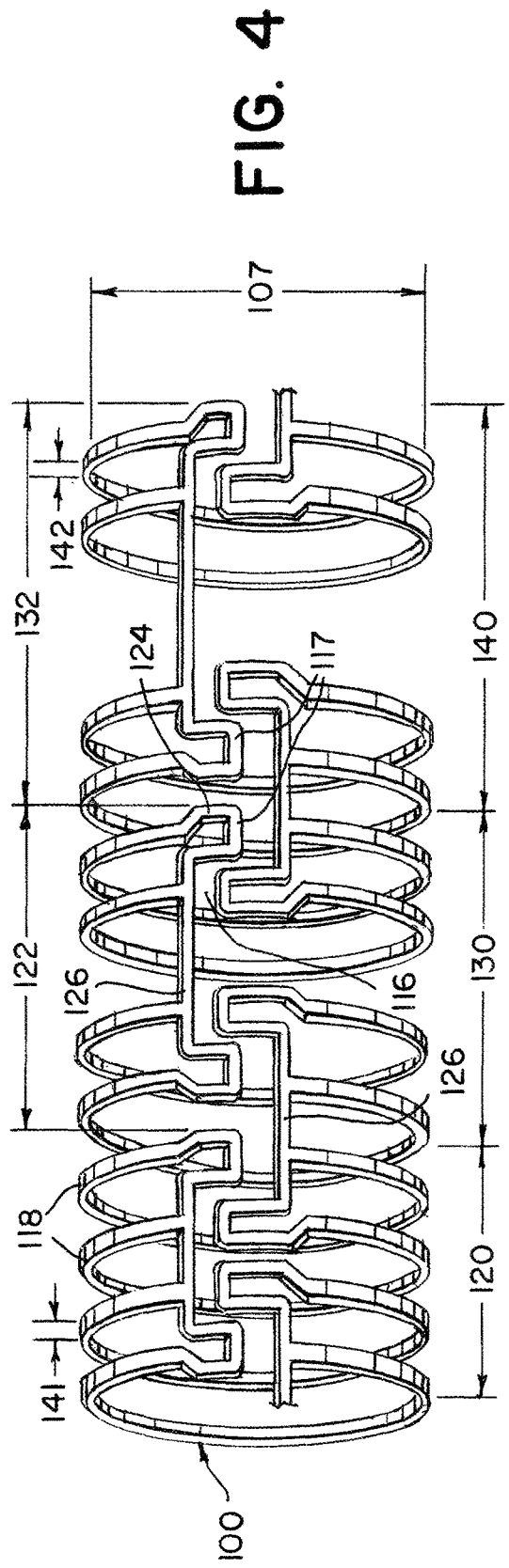

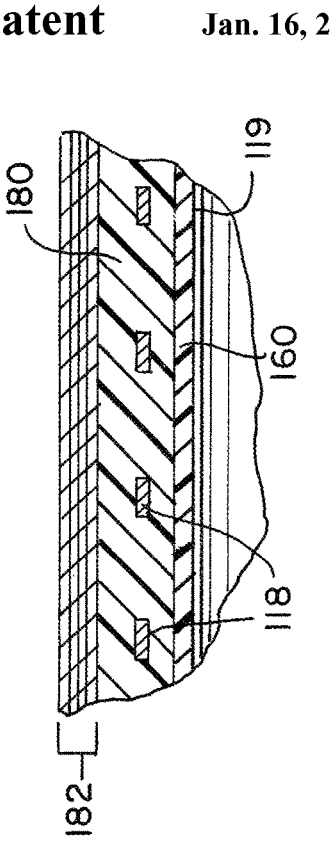
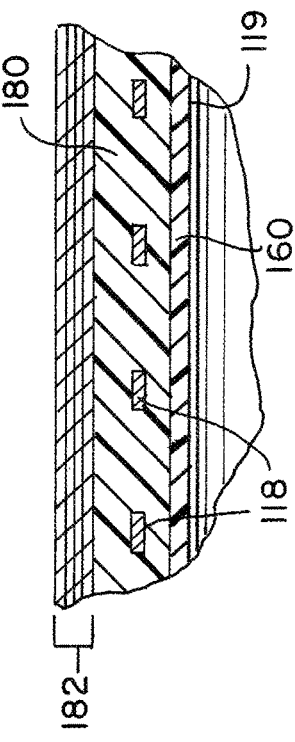
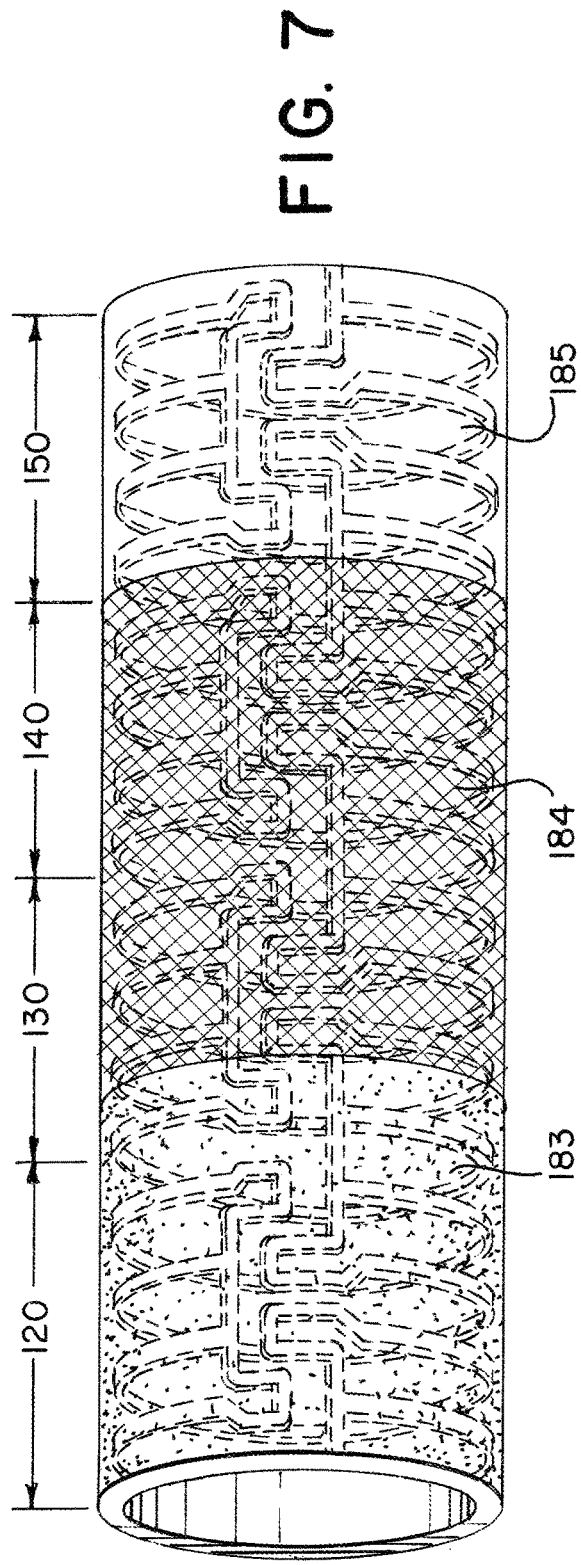

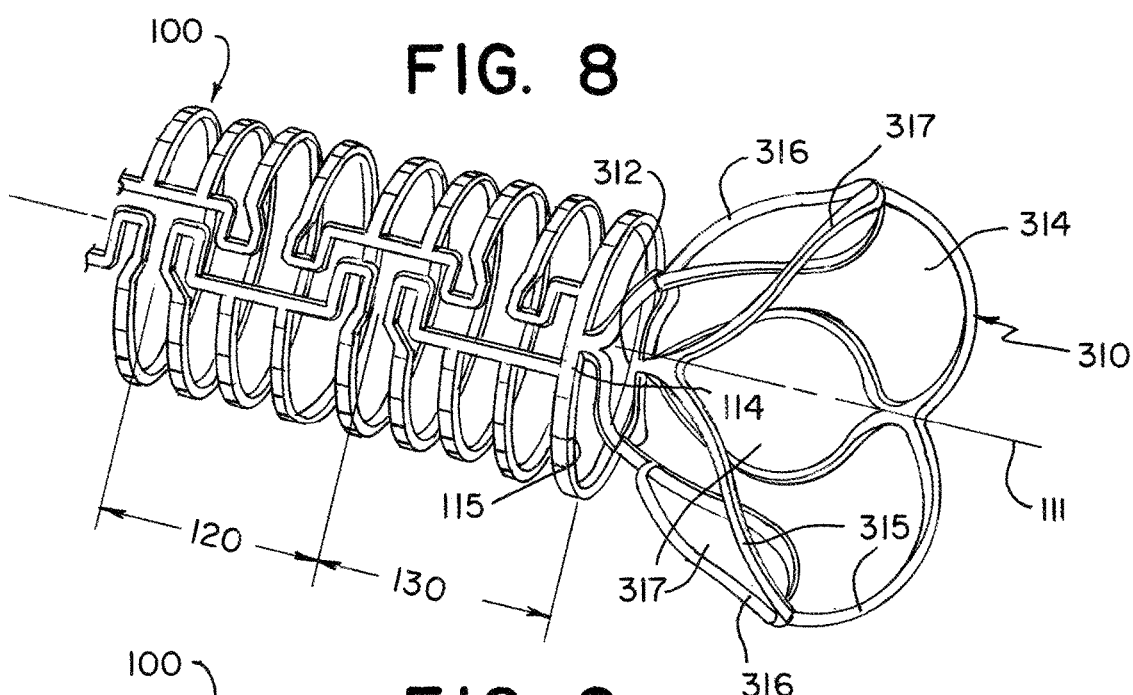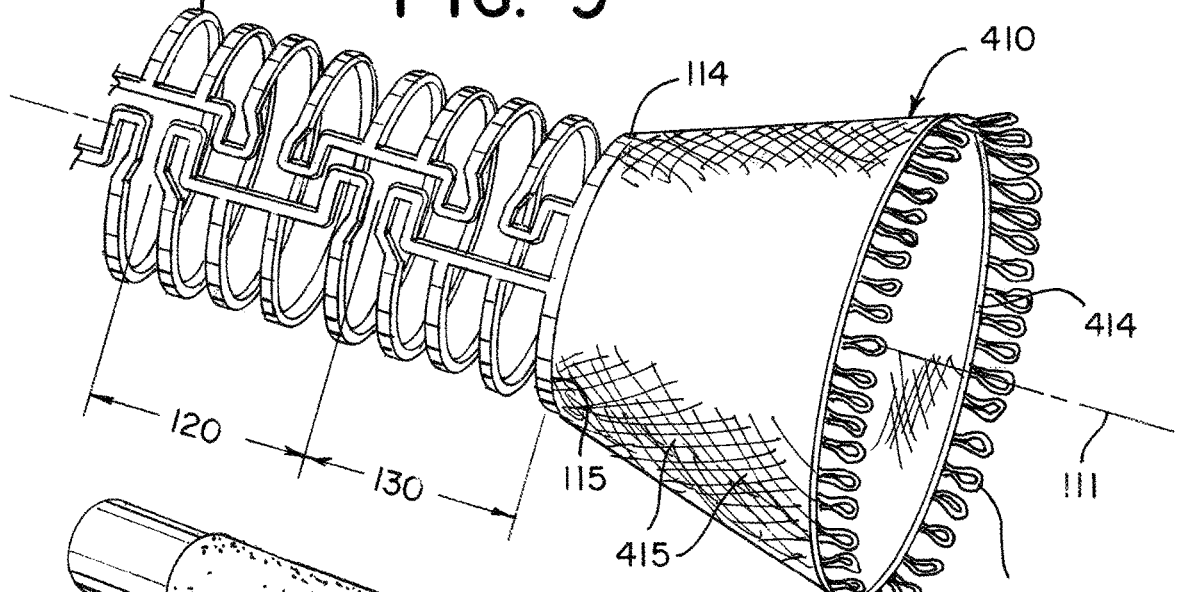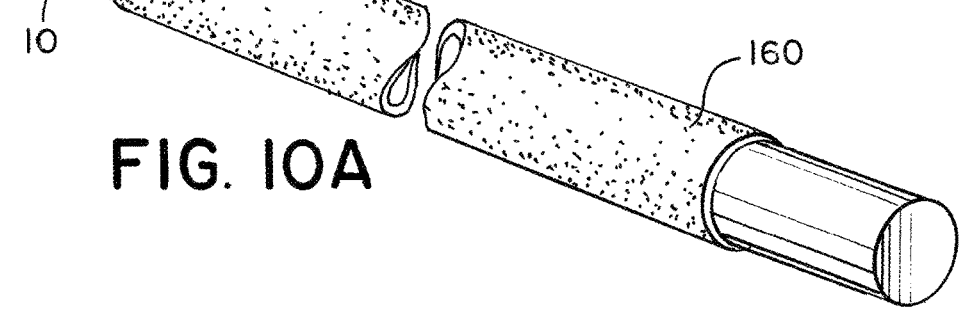

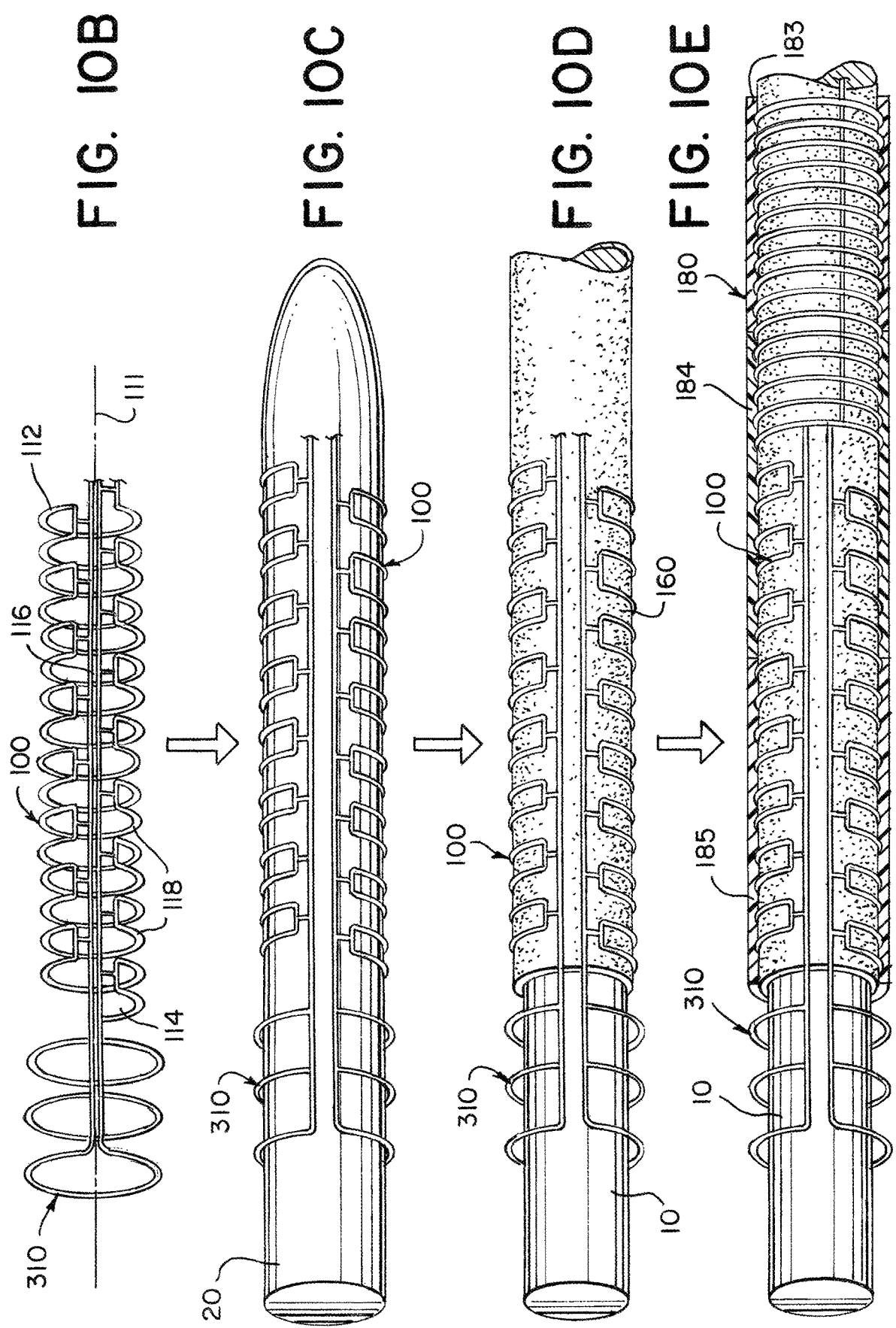

FLEXIBLE CATHETER SHAFT FRAME WITH SEAM

FIELD OF THE INVENTION

The present disclosure generally relates to devices and methods for accessing blood vessels during intravascular medical treatments. More specifically, the present disclosure relates to a catheter capable of radial expansion to facilitate the manufacturing and assembly of a catheter.

BACKGROUND

Catheters serve a broad range of functions in intravascular medical treatments. They are typically a thin tube manufactured from medical grade materials that can be inserted into a body and can be used to deliver drugs or other devices, perform surgical procedures, remove blockages from vessels, and a variety of other purposes.

There are a number of access challenges that can make it difficult to access a target site. Distant areas such as the neurovascular bed are challenging with conventional technology, as the target vessels are small in diameter, remote relative to the site of insertion, and are highly tortuous. Aspiration and/or access catheters for removing vessel occlusions in these areas need to be capable of enduring high flexure strains without kinking and progress through loops and increasingly smaller vessel sizes without causing trauma in order to access a target site. It is not unusual that a catheter will have to navigate windy pathways with multiple loops, where vessel segment can have several extreme bends in quick succession over only a few centimeters of travel.

The catheters must also have good compressive stiffness (for pushability, and stability and integrity when clot retrieval devices are withdrawn into them) and good tensile stiffness (to avoid stretching and deformation when placed in tension, such as when being retrieved into an outer sheath while holding a large clot). Managing the stiffness transitions from proximal to distal sections to avoid kinking is critical for these devices. The catheters must also allow for the easy transmission of other devices through the internal lumen. For these reasons trackability, flexibility, kink-resistance, and internal lubricity are often key design parameters associated with catheters used in these procedures. However, it can be tricky for designers of traditional catheters to combine these characteristics effectively without large trade-offs.

By modifying the material or adjusting the way a catheter is manufactured, it is possible to tailor the stiffness of different sections of the catheter for particular applications. Many current catheters control transitions from stiffer materials to softer materials by changing the configuration of a braided member backbone (changing the braid PIC count or coil pitch), utilizing a custom machined metallic support frame backbone, and/or by changing the durometer hardness of the surrounding polymeric materials. Coils of the braided wires used to reinforce the catheter shaft are often a continuous metallic super-elastic or stainless steel of very fine size which can be prone to kink and difficult to manufacture with the consistency needed for a uniform product. These materials can also add considerable cost and complexity.

The easy delivery of auxiliary devices (such as guidewires, microcatheters, clot retrieval/stentriever devices, etc.) through the internal lumen without excessive friction from binding must be considered. Many contemporary devices attempt to utilize an internal low friction liner to greatly enhance the lubricity of the catheter lumen. Such devices can be complicated to manufacture, since the inner diameter of the braid or metallic support frame backbone must be roughly the same or slightly smaller than the outer diameter of the inner liner on a mandrel during construction. Current backbone designs do not allow for the radial expansion necessary to slide over the liner during assembly without excessive friction.

The present designs are aimed at providing an improved catheter support frames and manufacturing methods to address the above-stated deficiencies.

SUMMARY

The innovations of this disclosure involve controlling the axial and lateral stiffness along the length of a catheter shaft and allowing the underlying support tube of the shaft to be radially expandable for assembly over a liner on a mandrel during manufacture. The catheter shaft tube can, for example, be cut from a hypotube into an axial series of circumferentially discontinuous ribs. The ribs can form an interlocking structure to give the shaft good resistance to both tensile elongation and compressive shortening while maintaining excellent lateral flexibility. Alignment of the circumferential discontinuities of the ribs can form longitudinal seams which allow the frame of the shaft to be expanded for ease of assembly with a low friction inner liner. The designs can manage stiffness transitions along the length of the shaft to avoid kinking by changing the configuration the features cut into the support tube over different axial segments of the shaft.

The catheter can have a shaft comprising a support tube, a proximal end, and a distal end. The support tube can have an inner liner disposed around a longitudinal axis. The support tube can have an axial series of interlocking segments formed from a plurality of circumferentially discontinuous ribs. This structure can create a substantially tubular profile along the longitudinal axis and define a lumen through the inner liner extending therethrough. In some examples, a spine can connect each of the plurality of ribs, with the spine following a non-linear profile around and along the axis of the support tube due to the circumferential discontinuities in the ribs.

The circumferentially discontinuous ribs of the support tube can form one or more axial seams in the support tube due to the relative longitudinal alignment of the axial splits in the ribs of the interlocking segments. In this way the support tube can radially open along the seam similar to a clamshell. The support tube can have a nominal, unexpanded inner diameter equal to or slightly less than the outer diameter of the inner liner prior to assembly. When expanded, the support tube can have an expanded inner diameter that is slightly larger than the outer diameter of the inner liner.

The spacing between adjacent interlocking segments can also be varied to tailor the catheter stiffness in different axial sections of the support tube. In one example, a first segment pitch measured between a first pair of adjacent interlocking segments can be the same as a second segment pitch measured between a second pair of adjacent interlocking segments. In another example, a first segment pitch measured between a first pair of adjacent interlocking segments can be different than a second segment pitch measured between a second pair of adjacent interlocking segments.

The manner in which the interlocking segments fit together around the axial seam or seams can take multiple forms. In one example, each of the axial series of interlocking segments can have a top half which can have a pair of inset teeth extending from respective ribs. Opposing this, the interlocking segments can have a bottom half with a pair of outset teeth extending from respective ribs which can define and bound a reception space between them. In some cases, the inset and outset teeth of the interlocking segments can have a triangular, quadrilateral, or other polygonal shape. In other examples, the teeth can form substantially L-shaped projections.

The apposition between the reception spaces of the bottom half and the inset teeth of the top half can be configured so the halves are in complimentary engagement with one another. When the support tube is assembled, this engagement creates the aligned gap of the one or more axial seams. The gap can be defined by the perimeter of the interface between the reception spaces of the bottom half and the inset teeth of the top half so that the seam or seams are continuous down the long axis of the support tube. When the seam follows this perimeter around the projections of the teeth along the axis, it can have a circumferentially and axially non-linear profile. The spine can also follow a non-linear path alternating between the top half and the bottom half along the ribs.

The distal end of the support tube can be configured to have any of a number of different tips or mouths attached depending on the objectives of a given procedure. In one case, the distal end can feature a face approximately perpendicular to the longitudinal axis. The face can be the distalmost rib, or a more specific ringed bracket. Such a face can allow for the attachment of therapeutic tips, expandable mouths, or other similar devices.

In other cases, a flexible support tube for a catheter shaft body can have a laser cut framework of struts forming substantially circular ribs distributed along a longitudinal axis of the support tube. The ribs can have one or more circumferential discontinuities around the circumference of the support tube. To link individual ribs, a spine can extend the length of the long axis of the support tube, navigating around the circumference of the tube and the gaps created by the discontinuities in the ribs. The distal end of the support tube can have a face configured for connecting catheter tips or mouths for conducting intravascular procedures.

The circumferential discontinuities in the ribs can create gaps which can be aligned to form one or more axial seams. The continuity the one or more seams can give some radial expansion capability to the support tube. This expansion can allow the support tube to be sized with a nominal inner diameter smaller than the outer diameter of an inner low friction liner. The support tube can then be expanded to slide over the liner on a mandrel as the catheter is assembled during manufacture.

The ribs of the framework of struts can be grouped to form an axial series of interlocking segments having a substantially tubular profile along a longitudinal axis. The interlocking segments can each have a top half and a bottom half. In some examples, the halves can be divided by a plane passing through the longitudinal axis and at least a portion of one of the one or more seams that is parallel to the axis. In some examples, a pair of inset teeth can extend from respective ribs of an interlocking segment on the top half. In a similar way, the corresponding bottom half of the same interlocking segment can have a pair of outset teeth extending from respective ribs and bounding a reception space.

The interlocking segments can be aligned such that each pair of inset teeth of the top half and each pair of outset teeth of the bottom half are in apposition to one another but are circumferentially separated from one another by the one or more axial seams when the support tube is assembled. As a result, the teeth can fit together like a zipper but not be fixedly connected to each other. The inset teeth of the top half can reside in the reception space created by the outset teeth of the bottom half. This overlapping engagement of the inset teeth into the reception space of the outset teeth can also limit the axial expansion of the support tube if the teeth are shaped such that there is a physical stop to expansion.

The inset teeth of each top half and the outset teeth of each bottom half of the interlocking segments can have projections normal to the longitudinal axis of the support tube. In other examples, the teeth can have projections parallel to the longitudinal axis or projections both parallel and normal to the axis. These shapes, combined with the overlap of the teeth into the reception spaces, can mean the one or more axial seams are a continuous gap defined by the perimeter of the interface of the outset teeth of the bottom half with the inset teeth of the top half of the interlocking segments. This perimeter can give the one or more axial seams a circumferentially and axially non-linear profile. The seam allows the support tube to radially expand while limiting the total expansion due to the engagement of the teeth. The engagement of the teeth can also limit any axial expansion of the support tube.

Dimensions of the support tube structure can also be varied to change the stiffness profile in different portions of the catheter. For example, a first rib width of a rib can be the same or different than a second rib width of another rib. Similarly, a first segment pitch measured between a first pair of adjacent interlocking segments can be the same or different than a second segment pitch measured between a second pair of adjacent interlocking segments.

Other processing beyond dimensional aspects can also be used to tailor the stiffness and bending flexibility of the catheter. For example, a series of polymeric jackets can be reflowed over the support tube to bond the underlying structure and create the outer surface of the catheter body. These outer jackets can have varying durometer hardness to create a proximal portion with more column stiffness and transition into a distal portion with more lateral flexibility.

Also included can be a method for manufacturing a catheter. The method can include the step of positioning a low friction inner liner on a first application mandrel. The liner can be PTFE or a like polymer.

Another step can involve forming a support tube having an axial seam allowing radial expansion of the support tube. In some examples, the support tube can be machined from a hypotube of a shape memory superelastic alloy such as Nitinol (NiTi) to have an unexpanded inner diameter equal to or slightly smaller than the outer diameter of the inner liner on the application mandrel.

The support tube can be laser cut to have a plurality of circumferentially discontinuous ribs disposed along the longitudinal axis between the proximal end and the distal end. The seam can be formed through the alignment of the circumferential discontinuities of the ribs along the axis. The ribs can thus also form a spine following a circumferentially and axially non-linear profile, alternating between the top half and the bottom half, which links each of the ribs.

The axial seam can be stretched by expanding the support tube on a substantially tubular second oversized mandrel. The oversized mandrel can have an outer diameter slightly larger than the outer diameter of inner the liner on the application mandrel. The method can then have the step of chilling the laser cut support tube on the oversized mandrel to a temperature at least below the Austenite finish ($A_f$) temperature of the alloy, and ideally at or below the Martensite finish ($M_f$) temperature. As an alternative, the support tube could be chilled to the desired temperature before expansion over the oversized mandrel. The second oversized mandrel can then be removed, and the radially expanded support tube positioned around the inner liner on the first application mandrel.

A plurality of outer polymer jackets can be reflowed or laminated to the support tube. The jackets can be in an axial series and have varying durometer hardness. In an alternate example, the jackets could be applied in a radial series or be a blend of materials. The reflow process can adhere the liner and support tube by flowing through the gaps between the ribs. The first application mandrel can then be removed once the structure has been bonded.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with reference to the following description in conjunction with the accompanying drawings. The drawings are not necessarily to scale, emphasis instead being placed upon illustrating the principles of the invention. The figures depict one or more implementations of the inventive devices, by way of example only, not by way of limitation.

FIG. 3 shows another example flat pattern for a support tube according to aspects of the present invention;

FIG. 4 is a view of an alternate expandable catheter support tube according to aspects of the present invention;

FIG. 5 shows a flexible catheter support tube having an outer polymer layer applied according to aspects of the present invention;

FIG. 6 illustrates a cross section from FIG. 5 showing an example outer polymer layer configuration according to aspects of the present invention;

FIG. 7 is a view of an alternative outer polymer layer configuration according to aspects of the present invention;

FIG. 8 is a view of an expandable catheter support tube having an attached expandable distal tip according to aspects of the present invention;

FIG. 9 shows another example of an expandable catheter support tube having an attached expandable distal tip according to aspects of the present invention;

FIGS. 10a-10e are illustrations of a possible manufacturing method for an expandable catheter support tube according to aspects of the present invention.

DETAILED DESCRIPTION

The objectives for the designs presented herein can be for a variably flexible and kink-resistant elongated catheter for vascular applications. The designs are flexible enough to access remote vessel occlusions but also benefit from good compressive and tensile stiffness. The designs can have proximal and distal ends and a laser cut support tube frame extending there between. The support tube frame can have an interlocking structure of ribs with at least one continuous split seam to allow some radial expansion during the manufacturing process while maintaining longitudinal stiffness. A low friction inner liner can be disposed on the interior surface of frame section. An outer polymer layer or laminating jacket can coat or encapsulate the struts of the frame, preventing disengagement of the interlocking structure while the catheter is pushed through tortuous anatomy. A distal face can allow for connecting any of a number of catheter tips, such as expandable funnel mouths for aspiration and clot retrieval.

The catheter can also be compatible with relatively low-profile access sheaths and outer catheters, so that a puncture wound in the patient's groin (in the case of femoral access) can be easily and reliably closed. While the following description is in many cases in the context of mechanical thrombectomy clot retrieval or other treatments in the neurovascular bed, the devices and methods described may be easily adapted for other procedures and in other body passageways as well.

Specific examples of the present invention are now described in detail with reference to the Figures, where identical reference numbers indicate elements which are functionally similar or identical. Accessing the various vessels within the vascular, whether they are coronary, pulmonary, or cerebral, involves well-known procedural steps and the use of a number of conventional, commercially available accessory products. These products can involve angiographic materials, rotating hemostasis valves, luers, and guidewires as widely used in laboratory and medical procedures. Though they may not be mentioned specifically by name, when these or similar products are necessarily employed in conjunction with the devices and methods of this invention in the description below, their function and exact constitution are not described in detail.

Figure 1:
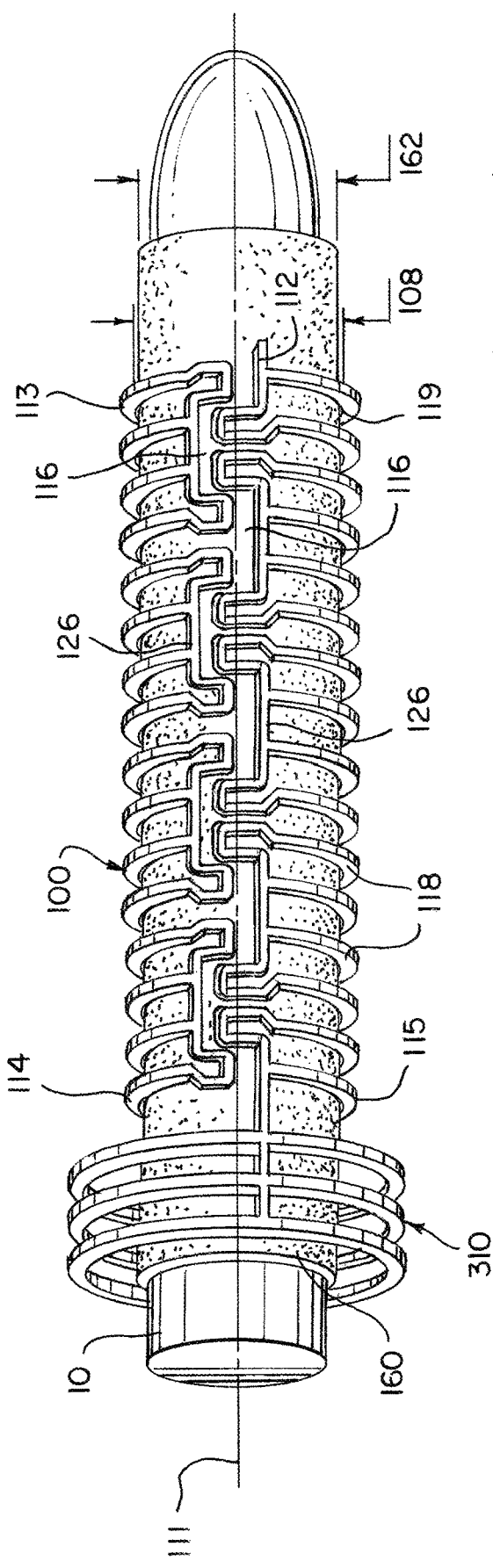
FIG. 1 is a view of an expandable catheter support tube on a mandrel according to aspects of the present invention.

Turning to the figures, in FIG. 1 there is illustrated a view of a catheter shaft support tube frame 100 for use in intravascular procedures in the vessels of a patient. The support tube is shown situated around a low friction inner liner 160 on a mandrel 10. The support tube 100 can generally be a tubular framework of struts between a proximal end 112 and a distal end 114 and have an inner lumen 119. A plurality of ribs 118 can form an extending axial series around the longitudinal axis 111. The struts can, for example, be laser cut from a hypotube. In another example, the support tube can be an injection molded polymer supporting structure. Features can also be incorporated into the strut framework which bias bending about certain planes or encourage twisting to reduce the imparted strains. In this way the catheter can maintain excellent lateral flexibility but will not tend to expand in tension or kink in compression.

The ribs 118 can be circumferentially discontinuous such that a longitudinal seam 116 splits the structure of the support tube 100 to allow for some radial expansion. Radial expansion can be beneficial, for example, during manufacturing when the laser cut support tube structure can be expanded to fit over the inner liner 160 or other layers on a supporting mandrel 10 as shown here. Without this ability to expand over the liner, there would be too much friction to effectively slide the frame over the liner/mandrel pair during assembly. Furthermore, if the support tube were sized larger than the diameter of the liner from the outset it would not sit concentrically on the liner and the wall thickness of the resulting catheter would be too large.

The support tube 100 can then have an expanded inner diameter 108 larger than the outer diameter 162 of the liner 160 on the mandrel. In this unrestrained state, the expanded ID 108 can be only slightly larger (0.001 inches, or up to 0.002-0.003 inches) than the OD if the liner.

Although the seam 116 can be continuous along the entire length of the support tube 100, a spine 126 can exist through the continuous running of the ribs 118 circumferentially on radially opposing sides of the seam. The spine 126 links the structure longitudinally but can allow for greater flexibility than would exist with, for example, a continuous and linear spine member running the length of the support tube 100 parallel to the longitudinal axis 111.

In some instances, the support tube 100 can be formed integrally with an expandable tip section 310 which can expand to a larger radial size when deployed from the distal end of a sheath or outer catheter. An enlarged tip can offer improved aspiration efficiency and can also allow for the gradual compression of a captured clot once it has been dislodged from the vessel and ingested.

Figure 2:
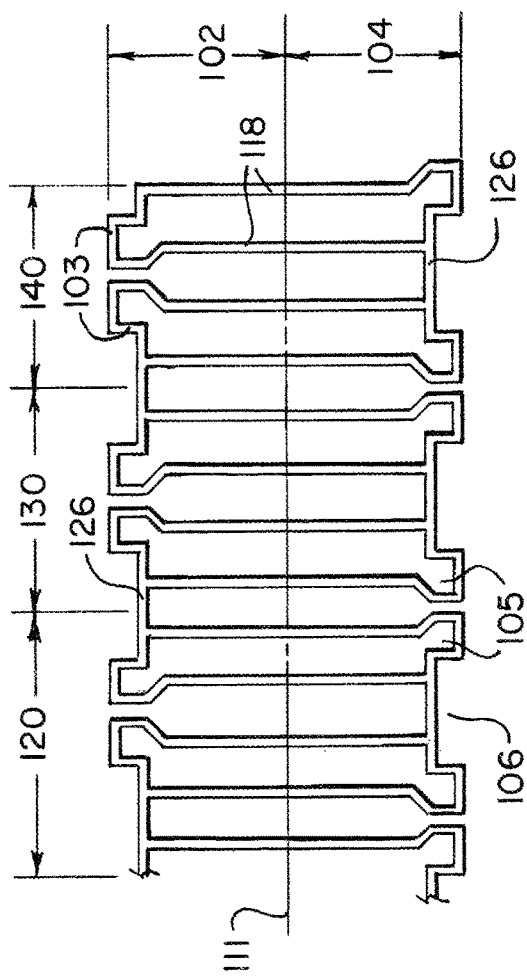
FIG. 2 is a representation of a flat pattern of FIG. 1 showing the top and bottom halves of the interlocking segments according to aspects of the present invention.

An example of a flat cut pattern for the support tube 100 from FIG. 1 is shown in FIG. 2. The pattern of ribs 118 can form a series of interlocking segments 120, 130, 140. The interlocking segments can be axially symmetric with each other as shown, or the pattern can be cut so there is irregularity and the segments are not symmetric. The longitudinal axis 111 can divide the pattern of interlocking segments 120, 130, 140 into a top half 102 and a bottom half 104. Both halves can have features configured to interlock with the other half when the tube is assembled, creating the seam 116 while resisting axial expansion and improving backup support for the catheter. Axial rigidity can be aided by the spine 126 linking the ribs 118 and following a non-linear path alternating between the top half 102 and bottom half 104 of the support tube 100.

The top half 102 of the interlocking segments, for example, can have a pair of inset teeth 103 cut in a shape that is primarily square as shown. Similarly, the bottom half 104 of the segments can have a pair of outset teeth 105. The outset teeth can border a reception space 106 for each interlocking segment where the inset teeth 103 can engage. In other examples, the teeth can have a triangular, quadrilateral, or other polygonal shape which can interlock and also improve the torque response of the catheter.

It can be appreciated that the reception space 106 for coupling the inset teeth 103 of the top half 102 and the outset teeth 105 of the bottom half 104 can be sized differently for differing interlocking segments 120, 130, 140 so that the size of the gap created by the inset teeth and reception spaces can be varied depending on the design parameters for different sections of the support tube 100. When secured together, the interlocking segments can therefore influence flexibility and/or bias bending of the assembly along certain planes.

Bending stiffness of the support tube 100 can also be tailored either through a combination of varying the cut width and rib width. Where the cut width is kept constant (for instance, the width of a laser beam) the rib width can be varied to tailor bending stiffness. Where the cut width is varied, the rib width can be kept constant or varied and the laser can be used to remove material. It is appreciated that by using a cut width equal to that of the laser beam, no pieces of material are removed, and the cost of manufacture is greatly reduced. On the other hand, by using the laser to remove pieces of material, greater variation in shaft design can be achieved. It is also appreciated that combination of both approaches may be used so the shaft incorporates more cost-effective cutting/processing at the proximal end and more costly approaches are kept distally where more complicated cuts can be required to achieve the desired flexibility performance. For example, a proximal section of the shaft may be cut from SS and be joined to a distal section cut from a superelastic alloy such as NiTi. This construction can reduce overall cost while affording the benefits of NiTi to the distal end of the device, where it is required for enhanced resilience in tight bending curves and also to provide some expansion and recovery characteristics. For such a device, the SS and NiTi sections can be joined by welding directly, by welding to a more weldable intermediate metal such as a platinum marker band. As an alternative, laser cut interlocking features can hold both cut tube sections together in the longitudinal direction. An outer membrane cover or jacket can secure the tubes together in a radial direction.

In some examples, the small size of the axial and radial gaps between the teeth of the interlocking segments can provide resistance to elongation and/or compression of the support tube while maintaining lateral flexibility required to navigate through the vasculature. The support tube can be prevented from stretching when it is being withdrawn back into an outer catheter and maintain stability against bunching up when a stentriever or another device is being withdrawn through the lumen.

FIG. 3 shows an alternate flat pattern example. The shown pattern has inset teeth 103 and outset teeth 105 that are substantially L-shaped projections 121 or variations thereof, which can orient the interlocking teeth in both the circumferential and longitudinal direction. The discontinuity of the seam allows the catheter to have a much greater freedom to flex than would be the case if a continuous and rigid spine member were used to connect the ribs. As compared with the pattern shown in FIG. 2, this tooth orientation can help to prevent hinging of the teeth 103, 105 when the catheter is navigated through tight bends in body passageways, at the cost of limiting some of the radial expansion capability of the support tube 100. After lamination of the outer jackets (not shown), this structure can provide a high effective modulus in both tension and compression and good integrity when retrieved against resistance.

Various dimensional parameters of the laser cut frame of the support tube 100 can also be adjusted to tune the catheter shaft for the desired flexibility performance as seen in FIG. 4. The pitch between interlocking segments can be designed such that the support tube 100 structure is stiffer and denser in more proximal areas and more flexible in distal regions. One method for measuring interlocking segment pitch can be the measured longitudinal distance between the distalmost rib 124 of one interlocking segment 130 and the distalmost rib 134 of an adjacent interlocking segment 140. The pitch can thus change the intermediate length of the split seam 116 for a given interlocking segment without impacting the interlocking capability.

For instance, a first segment pitch 122 for an interlocking segment 130 can be narrowed or shortened to provide better trackability and torque response near the proximal end 112 of the support tube. Similarly, near the distal end 114 where lateral flexibility is more of a concern, the support tube 100 can transition to a second segment pitch 132 of an interlocking segment 140 greater than the first segment pitch 122 to better optimize those physical capabilities. The change in pitch also changes the spacing between the teeth extensions 117 interlocking in adjacent reception spaces 106.

The segment pitch 122, 132 can alternatively be continuously varied along the longitudinal length of the support tube 100. As a result, adjacent interlocking segments 120, 130, 140 of the tube can become progressively closer together or further apart by a small but incrementally constant percentage with each successive segment. A continuously varied pitch can result in a more gradual stiffness transition along the length of the support tube 100 and provide rigidity while preventing the formation of kink points which can otherwise form at transitions with a higher stiffness gradient. This configuration can also aid in delivering a balanced and consistent push or thrust force through the length of the support tube 100 and ensure the operator receives decent tactile feedback from manipulating the catheter during a procedure.

Another design variable which can be altered to optimize the stiffness and flexibility of the support tube 100 is the width or cross sectional shape of the struts forming the ribs 118. For example, a smaller rib cross section can allow the support tube to flex more easily by affording greater space between ribs. As illustrated in FIG. 4, the rib width 141 of a strut of a more proximal interlocking segment 120 can be greater than a second, more distal rib width 142 of another interlocking segment 140.

The cut support tube 100 can have an outer polymer layer 180 or jacket around the ribs 118 of the interlocking segments, as shown in FIG. 5. The outer polymer layer 180 or jacket can be made of various medical grade polymers, such as PTFE, polyether block amide (Pebax®), or Nylon. Materials can be chosen, for example, so that more proximal segments are generally harder and less flexible (by durometer hardness, flexure modulus, etc.) as the proximal end 112 is approached to add column strength and pushability to the catheter. Similarly, softer, more flexible material segments can be used distally.

In one example, an outer jacket 180 can be reflowed over a laser cut hypotube and into the spaces between the ribs 118. After such a process, there can sometimes be material radially protruding at the location of the laser cut ribs 118. In this situation, the assembly can be pulled through a sizing die to remove any excess material above the struts such that the overall outer diameter of the support tube 100 shaft is consistent for a desired delivery profile. Alternatively, an uneven or ribbed profile may be desired to reduce friction between the outer surface of the catheter and an outer sheath or blood vessel.

In another example, the outer polymer layer 180 can be injection molded into the spaces of the support tube 100 during manufacturing. In a further example, the layer or jacket 180 can be adhered to the struts 118 of the support tube 100 using an adhesive with a primer component for bonding.

A cross sectional view through the wall of the catheter body from FIG. 5 is illustrated in FIG. 6. An inner liner 160 such as PTFE can offer the advantage of reducing friction with ancillary devices that are being advanced through the lumen 119 of the catheter. As mentioned, the outer polymer layer or jacket 180 can be reflowed, injection molded or otherwise adhered to the laser cut support tube structure.

The use of interior and exterior polymeric coatings, which may extend into, interface with, or blend with each other through the spaces in the laser cut support tube 100 aid in allowing the teeth of the interlocking segments to flex and interlock without plastic deformation. The ribs 118 can therefore have some independent flexing capability while having a limited constraint imposed by the outer jacket or jackets.

The layout and construction of the inner liner 160 and outer jacket 180 can be varied. For example, the outer jacket 180 material can extend radially inward to or beyond an inner surface of the support tube 100 or to an intermediate position within the inner diameter and outer diameter of the support tube interstitial of the ribs 118. Alternately, the outer jacket 180 may only be bonded to the surface of the outer diameter of the support tube. Having a jacket 180 which is bonded only to the outer diameter will allow the ribs 118 of the support tube to bend more freely, since a jacket extending more radially inward relative to the wall thickness of the support tube can stiffen the catheter. The unfilled gaps between support tube ribs 118 leave the ribs free to move axially. Other variabilities in stiffness can be achieved by having an outer jacket 180 composed of a composite series of radial jackets 182 each having a different thickness and/or being of differing materials. It can also be appreciated that the radial series of jackets 182 could be arranged in different manners for various axial segments of the catheter.

As previously discussed, the outer polymer layer can also be a formed from an axial series of polymer jackets. Different jackets or sets of jackets 183, 184, 185 can be disposed around the ribs 118 at discrete lengths along the axis of the support tube 100 in order to give distinct pushability and flexibility characteristics to different sections of the tubular portion of the catheter as shown in FIG. 7. The orientation shown is by demonstration only and not in way of limitation. FIG. 7 demonstrates a section of a support tube 100 with three polymer outer jacket layers, 183, 184, and 185, respectively. Factors, such as wall thickness and the length of the individual layers can be varied to lend stiffness or flexibility to portions of the support tube 100. The dimensions must also be selected so that the catheter meets the critical bend criteria as determined for the application.

In many examples, materials can be selected so the jacket layers 183, 184, 185 decrease in durometer distally. By configuring the jackets in an axial series, and using polymers with differing durometer hardness, it is possible to transition the overall stiffness of the catheter from being stiff and pushable at the proximal end to extremely flexible at the distal end. General selections for the outer jacket layers can be PTFE and Pebax®, but much more specialized materials or blends can be incorporated into specific axial sections of the support tube 100. In more proximal sections of the catheter where axial stiffness and resistance to collapse are important, the jacket segments can be made from a suitable robust polymer such as polyimide, nylon, polypropylene, or other materials with a higher density. For more distal sections where flexibility is required, the jacket segments can be for instance a polyurethane, PVC, low density polyethylene (LDPE), or other polymers of suitable modulus and softness. Blends, co-extrusions, and/or mixtures of these and other materials can also be used to obtain the right material properties for a particular segment.

Transitions between jackets can also be tapered or slotted to give a more gradual stiffness transition between abutting jackets in longitudinal series. When the jackets are applied through a reflow or lamination process, they can bond the underlying structure together and provide a smooth exterior finish. Slots or other features can then be added through machining or forming dies.

At the distal end 114 of the support tube 100, following the distalmost interlocking segment, the laser cut structure can have a face 115 approximately perpendicular to the longitudinal axis 111. The face can be another circular rib, a collar, or other suitable anchoring structure. Such a face can allow for the attachment of therapeutic tips, expandable mouths, or other similar devices.

FIG. 8 shows an example where the flat face 115 appears as a final independent circular rib. The rib of the flat face can have a single connection to the distalmost interlocking segment. In another variant, multiple connecting points can be disposed at various clocking positions around the axis The example expandable tip 310 shown in FIG. 8 is a framework of struts which can have four distal hoops 315 connected to four support arms 316. The support arms can each have a single attachment point to the distal face 115 at the distal end 114 of the support tube 100, or the connections can be shared. In one instance, a pair of hoops 315 can taper into a single support arm 316 so that there are two connections 180 degrees apart. The tip 310 can then hinge and bend along the plane created by these connections.

The tip 310 can be constructed from a shape memory allow and heat set so that it is capable of self-expanding when deployed from the distal end of an outer sheath or catheter. The support arms 316 can have enlarged cell openings 317 which can allow the arms to shorten and lengthen on opposing sides around the longitudinal axis 111 of the tip frame so that the device can track easily through an outer sheath or catheter in tortuous vessel paths. The branching of the support arm 316 struts can also allow the arms to torque and bend more freely than if a single strut without a cell 317 directly linked the distal hoops 315 with the distal face 115.

In many examples, the funnel shape formed by the tip 310 can be covered with another atraumatic polymer jacket or membrane (not shown). The enlarged mouth of the tip can improve aspiration efficiency, arrest unwanted flow, and lessen the risk of vessel trauma from snagging on vessel openings. When deployed, the tip 310 can match the vessel diameter and have sufficient radial force to seal with the vessel, or create enough of a flow restriction such that the majority of aspiration will be applied to blood and the clot distal of the mouth rather than fluid proximal of the tip.

In another example, the support tube 100 can have distal face 115 connected with an expandable mouth tip 410 which can have a radial array of struts or strands organized into a closed cell braid, as illustrated in FIG. 9. The braid can be connected to the flat face 115 of the support tube 100 and flare to a distal end 414, forming a substantially conical or funnel-like shape around the longitudinal axis 111 as shown when unconstrained and allowed to expand upon exiting an outer sheath or catheter.

The braid array can be made of wire or cut from a shape memory alloy such that the mouth can be heat set to self-expand from a collapsed delivery configuration to an enlarged deployed configuration. The mouth tip 410 can be adhered or otherwise bonded at the distal end 114 of the support tube 100. In one example, the braided tip 410 can be manufactured so as to have a single circumferential joint or ring collar for attaching the support tube 100. Alternatively, the individual strands of the braid can be bonded directly to the distal face 115 of the tube or embedded within a polymer jacket.

In another example, the expandable tip 410 can be a closed cell mesh array with a continuous polygonal pattern made of triangular or quadrilateral cell pores 415 which are interlocked through the vertices of the adjacent cells of the mesh. The pattern can be one of those commonly seen in stenting applications, where a minimally invasive mesh is used to support and hold open vessel passages. In one case, an elongated quadrilateral pattern forms cell pores 415 where local array peaks mark the shared vertices. The pattern can repeat in an axial and radial fashion and the distalmost array peaks of adjacent pores 415 can be joined by atraumatic curved distal hoops or crowns 412 to mark the distal end 414 of the expandable tip 410.

Figure 11:
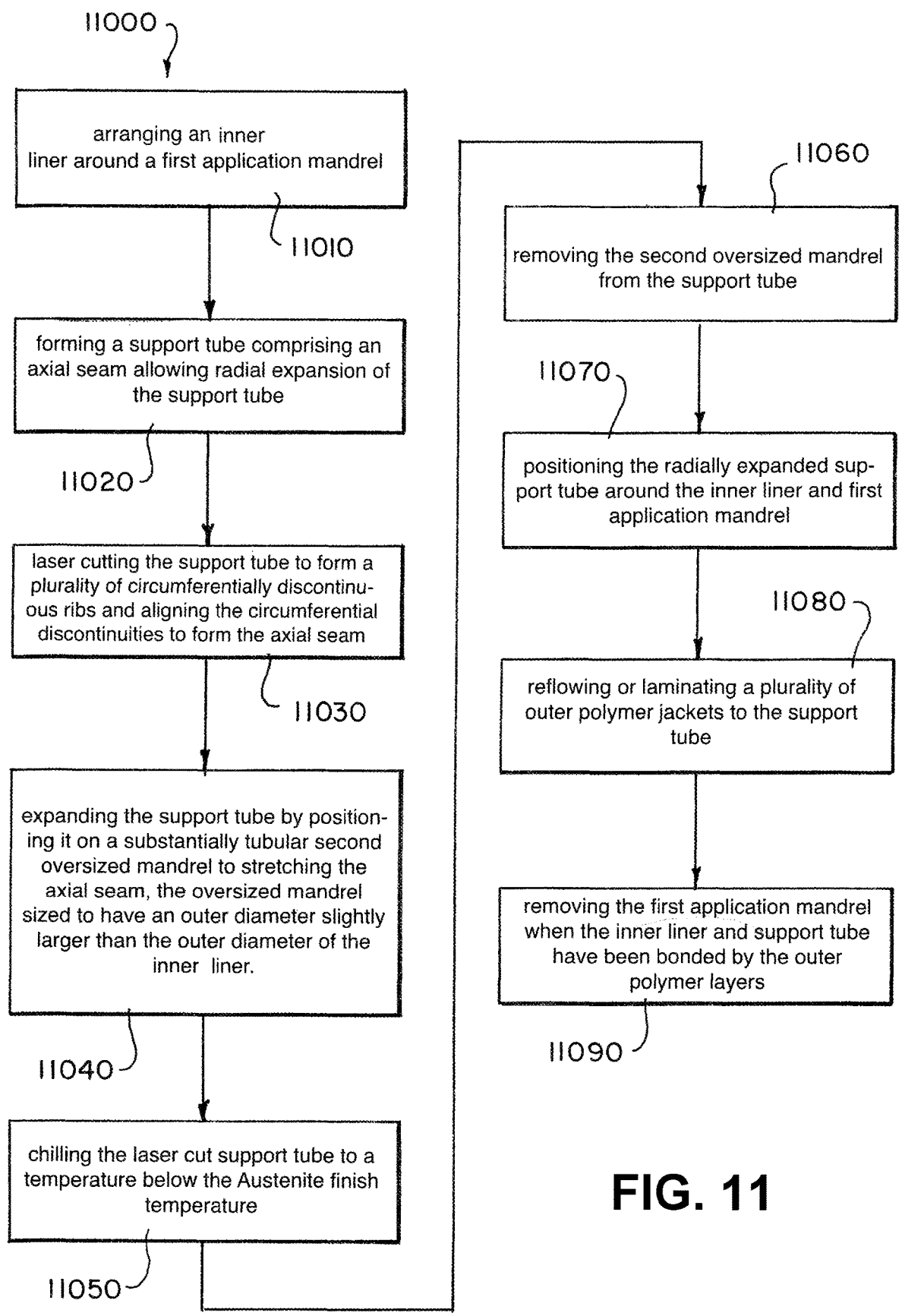
FIG. 11 is a process flow chart for the manufacturing method shown in FIGS. 10a-10e according to aspects of the present invention.

A method for manufacturing a catheter utilizing the disclosed expandable laser cut support tube 100 is graphically illustrated in FIGS. 10a-10e and further shown in the flow diagram in FIG. 11. FIG. 10a shows a low friction liner 160 positioned on a supporting mandrel 10. The mandrel can often be silver plated copper (SPC) as is commonly used for these applications. Alternatively, especially ductile materials (such as PEEK) can be used which stretch to neck down in diameter so that the mandrel can be removed after completion of the catheter assembly. Further mandrel materials can be nylon coated copper or nylon coated steel.

A laser cut support tube frame 100 is formed in FIG. 10b which has a continuous longitudinal split seam 116, allowing the frame of the support tube to expand radially in an elastic fashion. In some examples, the support tube frame 100 can be cut from NiTi or another shape memory superelastic alloy so that the solid state phase transformations can be designed to dictate the constrained and unconstrained diameters of the frame. This expansion allows the support tube 100 to have an inner diameter roughly the same size as the outer diameter 162 of the liner 160. Ribs 118 can be arranged and varied along the longitudinal axis 111 such that the support tube 100 has good pushability and column strength near the proximal end 112 and excellent lateral flexibility near the distal end 114. In some examples and expandable tip 310 can be formed or attached at the distal end 114 of the support tube 100.

In FIG. 10c the support tube frame 100 is radially expanded at the seam and slid over an oversized mandrel 20. The oversized mandrel 20 can be, for example, at least 0.005 inches greater than the outer diameter 162 of the inner liner 160 on the application mandrel 10. The support tube 100 can then be chilled to a lower temperature (ideally close to or below the Martensite Finish ($M_f$) temperature) to transform the support tube material to the martensitic phase. In another example, the support tube 100 can be chilled first and then expanded over the oversized mandrel 20. If kept chilled, the reversible solid state transformation to martensite can allow the support tube 100 to maintain its expanded shape when removed from the oversized mandrel 20.

Alternatively, the chilling steps can be eliminated by disposing a thin outer metal sleeve (not shown) around the oversized mandrel 20. The support tube 100 can be elastically expanded over the sleeve/oversized mandrel assembly and the oversized mandrel removed. The sleeve constrains the support tube radially so that it can then be slid over the inner liner 160 on the application mandrel 10. When the sleeve support is removed, the support frame 100 can contract down onto the inner liner 160.

The expanded support tube 100 can be slid over the inner liner 160 on the SPC application mandrel 10 as depicted in FIG. 10d. Without expanding the support tube, this step would generate too much friction to create a reliable and repeatable interface between the support tube and liner. Once in place and concentric with the liner 160, an outer polymer layer 180 can be applied over the support tube 100 (FIG. 10e). The layer 180 can be an axial series of separate polymer extrusions which can be reflowed or laminated in place as outer jackets 183, 184, 185. The applied heat can allow the outer polymer to fill the interstitial sites between the ribs of the support tube.

A similar process is outlined in the method flow diagram in FIG. 11. The method steps can be implemented by any of the example devices or suitable alternatives described herein and known to one of ordinary skill in the art. The method can have some or all of the steps described, and in many cases, steps can be performed in a different order than that disclosed below.

Referring to FIG. 11, the method 11000 can have the step 11010 of arranging an inner liner around a first application mandrel. The liner can be PTFE or a similar low friction material. The mandrel can be sized to be approximately equal to the desired inner diameter of the completed catheter. Step 11020 can then involve forming a laser cut support tube structure as described previously herein. The support tube can be cut from single continuous hypotube, which can be but is not limited to Nitinol or another shape memory superelastic alloy. The cuts can form a series of circumferentially discontinuous ribs, the discontinuities aligning to form one or more longitudinally continuous seams running the length of the support tube, as seen in FIG. 10*a* and step 11030. The ribs can be linked by a spine extending axially and following a circuitous route around the ribs of the support tube in a non-linear fashion on alternating sides of the seam. This structure can allow some radial expansion of the support tube while offering good axial resistance to both tensile and compressive loading. The inner diameter of the support tube can be equal to or slightly less than the outer diameter of the low friction inner liner, so the components sit concentrically when the catheter is assembled.

In step 11040, the support tube can be elastically expanded by stretching the axial seam so that the support tube can be placed on a second oversized mandrel. In some examples, the oversized mandrel can be sized so that the expanded inner diameter of the support tube frame is slightly larger than the outer diameter of the inner liner on the application mandrel. In some examples, the ID can be approximately 0.003-0.005 inches larger than the OD of the liner. Once the support tube is expanded on the oversized mandrel, it can be chilled to a temperature at least below the $A_f$ temperature, and ideally close to or below the $M_f$ temperature of the material to induce a phase change to martensite. The martensitic phase is thermodynamically stable, so the support tube can be kept chilled and will retain its expanded state when the second oversized mandrel is removed in step 11060.

The expanded support tube can then be slid over and positioned around the inner liner on the first application mandrel in step 11070. A series of outer polymer jackets of varying durometer hardness can then be reflowed to the support tube (step 11080). The jackets can be in an axial series, a radial series, or some combination. The flow of the jacket materials can allow them to encapsulate the ribs struts of the support tube and bond with the inner liner. The first application mandrel can be removed in step 11090 once the assembly is completed.

The invention is not necessarily limited to the examples described, which can be varied in construction and detail. The terms "distal" and "proximal" are used throughout the preceding description and are meant to refer to a positions and directions relative to a treating physician. As such, "distal" or "distally" refer to a position distant to or a direction away from the physician. Similarly, "proximal" or "proximally" refer to a position near or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A flexible catheter comprising a support tube, a proximal end, and a distal end, the support tube comprising:
   an inner liner disposed around a longitudinal axis of the support tube;
   an axial series of interlocking segments forming a substantially tubular profile along the longitudinal axis, the interlocking segments comprising a plurality of circumferentially discontinuous ribs, each interlocking segment comprising:
      a top half comprising a pair of inset teeth extending from respective ribs of the plurality of circumferentially discontinuous ribs; and
      a bottom half comprising a pair of outset teeth extending from respective ribs of the plurality of circumferentially discontinuous ribs and bounding a reception space;
   one or more axial seams formed by alignment of the plurality of circumferentially discontinuous ribs of the interlocking segments; and
   a spine axially linking the interlocking segments and axially linking each of the ribs of the plurality of circumferentially discontinuous ribs by forming an inner face of the reception space,
   wherein each rib of the plurality of circumferentially discontinuous ribs is substantially circular,
   wherein the spine follows a non-linear path alternating between the top half and the bottom half of the support tube, and
   wherein the one or more axial seams allow the support tube to be radially expanded to an expanded inner diameter larger than an outer diameter of the inner liner.

2. The catheter of claim 1, wherein reception spaces of the bottom half are configured to interface with the inset teeth of the top half such that the top half and bottom half are in apposition to one another and are radially separable from one another by the one or more axial seams when the support tube is assembled.

3. The catheter of claim 1, wherein the one or more axial seams are a continuous gap defined by a perimeter of the interface between reception spaces of the bottom half with the inset teeth of the top half.

4. The catheter of claim 1, wherein the inset teeth and outset teeth comprise a quadrilateral shape.

5. The catheter of claim 1, wherein the inset teeth and outset teeth comprise L-shaped projections.

6. The catheter of claim 1, wherein the inset teeth of the top half and the outset teeth of the bottom half comprise a projection parallel to the longitudinal axis of the support tube.

7. The catheter of claim 1, wherein the distal end has a face approximately perpendicular to the longitudinal axis configured for connecting to a catheter mouth configured for conducting intravascular procedures.

8. The catheter of claim 1, wherein a contour of the one or more axial seams follows a non-linear profile.

9. The catheter of claim 1, wherein a first segment pitch measured between a first pair of adjacent interlocking segments is different than a second segment pitch measured between a second pair of adjacent interlocking segments.

* * * * *